United States Patent [19]
Ando et al.

[11] Patent Number: 5,460,977
[45] Date of Patent: Oct. 24, 1995

[54] PEPTIDE HAVING ALLERGENICITY

[75] Inventors: Tohru Ando, Funabashi; Shigeru Ikeda; Yasushi Okumura, both of Tokyo, all of Japan

[73] Assignees: Torii & Co.; Asahi Breweries, Ltd., both of Tokyo, Japan

[21] Appl. No.: 211,295

[22] PCT Filed: Aug. 10, 1993

[86] PCT No.: PCT/JP93/01127

§ 371 Date: Mar. 30, 1994

§ 102(e) Date: Mar. 30, 1994

[87] PCT Pub. No.: WO94/04572

PCT Pub. Date: Mar. 3, 1994

[30] Foreign Application Priority Data

Aug. 14, 1992 [JP] Japan .................. 4-216955

[51] Int. Cl.$^6$ .............. A61K 38/00; C07K 5/00; C07K 7/00; C07K 17/00
[52] U.S. Cl. .............. 436/513; 436/63; 436/811; 530/324; 530/326; 435/29
[58] Field of Search .............. 435/29; 530/324, 530/326; 514/12–14; 436/513, 63, 811

[56] References Cited

FOREIGN PATENT DOCUMENTS

| 0445971 | 9/1991 | European Pat. Off. |
| 88/10297 | 12/1988 | WIPO |
| 92/04445 | 3/1992 | WIPO |
| 92/11859 | 7/1992 | WIPO |
| 93/08279 | 4/1993 | WIPO |

OTHER PUBLICATIONS

Hof, Wim Van't, et al., "Epitope mapping of the *Dermatophagoides pteronyssinus* house dust mite major allergen *Der p* II using overlapping syntheitc peptides", Molecular Immunology (1991), vol. 28, pp. 1225–1232.

*Primary Examiner*—Jill Warden
*Assistant Examiner*—Sheela J. Huff
*Attorney, Agent, or Firm*—Beveridge, DeGrandi, Weilacher & Young

[57] ABSTRACT

According to the present invention, a peptide which causes the blast formation of lymphocytes sensitized by mites is provided, and mite allergy is diagnosed by using the peptide. The present invention relates to a peptide, that is, pentadecapeptide and triacontapeptide, which causes the blast formation of lymphocytes sensitized by mites and to a diagnostic agent for mite allergy while uses the peptide.

8 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( x i ) SEQUENCE DESCRIPTION: SEQ ID NO:1:

```
Asp  Gln  Val  Asp  Val  Lys  Asp  Cys  Ala  Asn  Asn  Glu  Ile  Lys  Lys
1                  5                        10                       15
```

( 2 ) INFORMATION FOR SEQ ID NO:2:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( x i ) SEQUENCE DESCRIPTION: SEQ ID NO:2:

```
Gly  Val  Leu  Ala  Cys  Ala  Ile  Ala  Thr  His  Ala  Lys  Ile  Arg  Asp
1                  5                        10                       15
```

PEPTIDE HAVING ALLERGENICITY

The present invention relates to a peptide which causes the blast formation of lymphocytes of allergic patients sensitized with mite allergen. Such a peptide can be used for the diagnosis of mite allergy.

In order to diagnose so-called type I allergy, such as allergic asthma and allergic rhinitis, a method has heretofore been used which employs a causative antigen (i.e. allergen).

That is, there has been widely used a method wherein an allergen is injected intradermally or dropped onto slightly injured skin and the resulting skin reaction is observed to identify the allergen, or such a method as RAST, wherein allergen specific IgE in blood serum is detected in vitro.

In these methods of diagnosis, allergens extracted from naturally occurring substances have hitherto been used. That is, crude allergens extracted from allergen-containing substances, as pollen, house dust and mites, with, for example, the Coca solution (Practice Allergy, third edition, written by W. T. Vaughhan & J. H. Black) have been used. Consequently, these methods often cause side reactions and hence tend to lead to diagnosis of insufficient accuracy. Recently, for the purpose of obtaining pure allergens, a number of attempts have been made to prepare major allergens of pollen or mites by means of genetic recombination (R. Valena et al., Int. Arch. Allergy & Applied Immunol., 97, 287 (1992), Japanese Patent Application Nos. H-3-262538 and H-3-310069).

Mites are one of the most important allergens causing type I allergy. For preparing a mite allergen, there are known, as described above, a method which extracts it from mite bodies and a method which prepare it by genetic recombination. By the method of extraction from mite bodies, however, it is difficult to prepare the purified allergen in large quantity. By the method of preparing a mite allergen through genetic recombination, on the other hand, it is impossible to prepare solely the allergenic activity-bearing low molecular weight portion which constitutes a part of the major allergen protein of mites, unlike in the process of the present invention.

Accordingly, the present inventors have attempted to prepare a substance having allergenic activity easily and in a pure form by chemically synthesizing solely the allergenic activity-bearing portion of the major allergen protein of mites. Thus, the inventors have synthesized various parts of the amino acid sequence of Der f II, which is one of the major allergens of *Dermatophagoides farinae*, and resultantly found a peptide which has allergenic activity.

The cell which mainly participates in the humoral immunity of mammalia, including human beings, is a lymphocyte.

When the lymphocyte of a patient sensitized by an allergen is reacted with the allergen, the cell is stimulated to cause lively nucleic acid synthesis; that is, so-called blast formation takes place. As the result, the incorporation of thymidine, which is a constituent of nucleic acid, into the cell increases.

Making use of the above-mentioned phenomenon, the present inventors have made a thymidine labelled with radioactivity and the peptide of the present invention to react with the lymphocyte of a mite-allergic patient or a non-allergic subject. As the result, virtually no incorporation of thymidine to the lymphocyte of non-allergic subject was recognized, while a marked incorporation of thymidine into the lymphocyte of allergic patient was observed, revealing that blast formation took place.

This demonstrates that the peptide of the present invention was clearly recognized by the lymphocyte of a mite-allergic patient. In other words, by using the peptide of the present invention, the diagnosis of allergy becomes possible based on the fact that the lymphocyte of a patient sensitized by mites undergoes blast formation, whereas the lymphocyte of a non-allergic subject not sensitized by mites undergoes no blast formation.

According to the present invention, there is provided a peptide which causes the blast formation of lymphocytes represented by mites. In more particular, peptides represented by the following formulas I to V are provided.

A pentadecapeptide represented by the formula (SEQ ID NO:1)

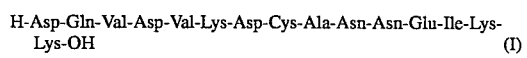

H-Asp-Gln-Val-Asp-Val-Lys-Asp-Cys-Ala-Asn-Asn-Glu-Ile-Lys-Lys-OH     (I)

wherein Asp, Gln, Val, Lys, Cys, Ala, Asn, Glu and Ile denote, respectively, the residue of aspartic acid, glutamine, valine, lysine, cysteine, alanine, asparagine, glutamic acid and isoleucine.

A triacontapeptide represented by the formula

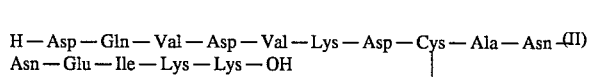

H—Asp—Gln—Val—Asp—Val—Lys—Asp—Cys—Ala—Asn— (II)
Asn—Glu—Ile—Lys—Lys—OH

H—Asp—Gln—Val—Asp—Val—Lys—Asp—Cys—Ala—Asn—
Asn—Glu—Ile—Lys—Lys—OH wherein Asp, Gln, Val, Lys, (Cys)$_2$, Ala, Asn, Glu and Ile denote, respectively, the residue of aspartic acid, glutamine, valine, lysine, cystine, alanine, asparagine, glutamic acid and isoleucine.

A pentadecapeptide represented by the formula (SEQ ID NO:2)

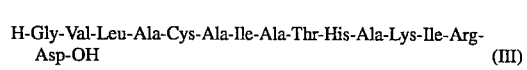

H-Gly-Val-Leu-Ala-Cys-Ala-Ile-Ala-Thr-His-Ala-Lys-Ile-Arg-Asp-OH     (III)

wherein Gly, Asp, Val, Lys, Cys, Ala, Ile, Leu, Thr, His and Arg denote, respectively, the residue of glycine, aspartic acid, valine, lysine, cysteine, alanine, isoleucine, leucine, threonine, histidine and arginine.

A triacontapeptide represented by the formula

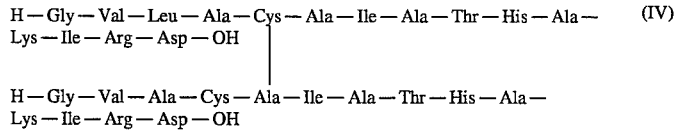

H—Gly—Val—Leu—Ala—Cys—Ala—Ile—Ala—Thr—His—Ala—     (IV)
Lys—Ile—Arg—Asp—OH

H—Gly—Val—Ala—Cys—Ala—Ile—Ala—Thr—His—Ala—
Lys—Ile—Arg—Asp—OH

wherein Gly, Asp, Val, Lys, (Cys)$_2$, Ala, Ile, Leu, Thr, His and Arg denote, respectively, the residue of glycine, aspartic acid, valine, lysine, cystine, alanine, isoleucine, leucine, threonine, histidine and arginine.

A triacontapeptide represented by the formula

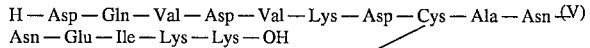
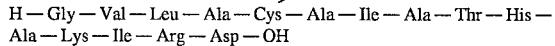

wherein Asp, Gln, Val, Lys, (Cys)₂, Ala, Asn, Glu, Ile, Gly, Leu, Thr, His and Arg denote, respectively, the residue of aspartic acid, glutamine, valine, lysine, cystine, alanine, asparagine, glutamic acid, isoleucine, glycine, leucine, threonine, histidine and arginine.

The peptide of the present invention may be prepared, in general, by using the method as described by R. B. Merrifield (J. Am. Chem. Soc., 85, 2149 (1963)), but it may also be prepared by using other known, equivalent methods of chemical synthesis.

The solid phase synthesis starts from a resin obtained by bonding to an appropriate resin through an ester linkage a protected amino acid obtained by protecting, with an appropriate protecting group, the α-amino group of the C-terminal α-amino acid of the peptide to be synthesized. The protecting group for the α-amino group may be, for example, tert-butyloxycarbonyl (Boc) or 9-fluorenylmethyloxycarbonyl (Fmoc), but it is not limited thereto. The resin used herein may be, for example, 4-(oxymethyl)phenylacetamidomethyl (PAM), 4-oxymethylphenyl (Merrifield) or 4-(4'-oxymethylphenoxymethyl)phenyl (Wang) resin, but it is not limited thereto.

All of the protected amino acids are of an L-configuration.

In the solid phase synthesis, the reactive side-chain functional groups of various amino acids must be protected by appropriate protecting groups. These protecting groups must continue to exist stably until the time when the peptide is cleaved from the resin at the final stage, to prevent side reactions from occurring at the site.

Specific examples of the protecting group for the amino group include the benzyloxycarbonyl (Z) and Boc group. Those for the carboxyl group include the benzyl (Bzl) and tert-butyl (But) ester group. Those for the hydroxyl group include the benzyl (Bzl) and tert-butyl (But) ether group. Those for the guanidine group include the 4-toluenesulfonyl (Tos) and 4-methoxy-2,3,6-trimethylbenzenesulfonyl (Mtr) group. Those for the imidazole group include the trityl (Trt) group. Those for the sulfhydryl group include the trityl (Trt) and tert-butyl (But) thioether group. The present invention, however, is not limited to these protecting groups.

In a reaction vessel was placed 0.5 g of Fmoc-amino acid-Wang-resin, and then protected amino acids were coupled in order by following the process steps described below, to prolong the peptide chain.

The first step: 0.5 g of Fmoc-amino acid-Wang-resin is placed in a reaction vessel, then 6–8 ml of N,N-dimethylformamide (DMF) is added thereto, the resulting mixture is shaken for one minute and the DMF is discarded. This operation is repeated 3 times. The second step: 6–8 ml of a 20% piperidine (PIP)/DMF solution is added, the resulting mixture is shaken for 3 minutes and then the DMF is discarded. This operation is repeated twice. The third step: 6–8 ml of a 20% PIP/DMF solution is added, the mixture is shaken for 20 minutes, and then the 20% PIP/DMF solution is discarded. The fourth step: 6–8 ml of DMF is added, the mixture is shaken for one minute and then the DMF is discarded. This operation is repeated 3 times. The fifth step: 6–8 ml of N-methylpyrrolidinone (NMP) is added, the mixture is shaken for one minute, and then the NMP is discarded. This operation is repeated 3 times. The sixth step: 3–6 equivalents of Fmoc-amino acid, N,N'-diisopropylcarbodiimide (DIPCI), N-hydroxybenzotriazole (HOBT) and 6–8 ml of NMP are added, the resulting mixture is shaken for 60 minutes, and then filtered to discard the unreacted Fmoc-amino acid and the coupling reagent. The seventh step: 6–8 ml of NMP is added, the resulting mixture is shaken for one minute, and then the NMP is discarded. This operation is repeated 3 times. The eighth step: the sixth step and the seventh step are repeated.

The N-terminal protected amino acid of the peptide to be synthesized is coupled, the Fmoc group is removed by following the first step through the fifth step, and then the peptide resin is dried overnight over phosphorus pentoxide under vacuum. The peptide was cleaved from the resin by using an appropriate cleavage reagent. For example, trifluoroacetic acid (TFA) containing 5% of phenol (PhOH) is added to the reaction vessel containing the peptide resin, the resulting mixture is shaken at room temperature for one hour and then filtered, and the resin is washed thoroughly with TFA. The filtrate and the washings were collected, concentrated, and diethyl ether was added to the residue to obtain a crude peptide as a solid.

Purification of a peptide in which the sulfhydryl group of cysteine is free was achieved by subjecting the crude peptide to a preparative high performance liquid chromatography (HPLC) using a μ-Bondasphere C 18 reversed phase column (1.9×15 cm). The crude peptide was dissolved in a minimum amount of acetic acid, then injected directly into the column, and eluted under the condition of linear gradient of 10–30% acetonitrile/0.01N hydrochloric acid at a flow rate of 10 ml/min. Purification of a peptide having a symmetrical disulfide linkage was achieved, for example, by air-oxidation of the crude peptide in an aqueous potassium hydrogencarbonate solution (pH 8), then adjusting the pH of the reaction mixture to 4 with acetic acid, and subjecting the mixture to preparative HPLC.

Synthesis and purification of a peptide having an unsymmetrical disulfide linkage was achieved by a method as described by O. Plaux in Int. J. Peptide Protein Res., 29, 162 (1987). Thus, a peptide in which the sulfhydryl group of cysteine is free and a peptide containing S-3-nitropyridinesulfenyl (Npys)-cysteine, or alternatively, two kinds of peptide in which the sulfhydryl group of cysteine is free were reacted, for example, in an aqueous potassium hydrogencarbonate solution (pH 8), then adjusting the pH of the reaction mixture to 4 with acetic acid, and subjecting the mixture to preparative HPLC in the same manner as described above.

The purity of the individual peptide was determined by analytical HPLC. The results of amino acid analysis were in good agreement with theoretical values.

According to the present invention, a peptide is obtained which causes the blast formation of lymphocytes of allergic patients sensitized by mite allergen, and the peptide can be used for the diagnosis of mite allergy with satisfactory results.

The present invention is illustrated below with reference to the following Example, but it is in no way limited thereby.

EXAMPLE 1

Preparation of Pentadecapeptide of Formula I

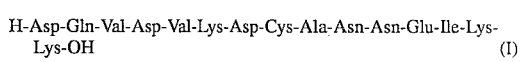

In a reaction vessel was placed 0.5 g of Fmoc-Lys(Boc)-Wang-resin (content: 0.17 mmole/0.5 g), and treated by following the solid phase synthesis steps as described below. The Fmoc group was removed with 20% PIP/DMF (steps 1–5) to protonate the amino group, and then Fmoc-amino acid derivative was coupled in order by the DIPCI-HOBT method (steps 6, 7 and 8). The Fmoc-amino acid, DIPCI and HOBT were added and reacted, in step 6 as follows: Fmoc-Lys(Boc)-OH (238 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Ile-OH (180 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Glu(OBut)-OH (217 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Asn-OH (177 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Asn-OH (177 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Ala-OH (159 mg, 0.5 mmole), HOBT (77 mg, 0.5 mmole), DIPCI (63 mg, 0.5 mmole) and NMP (6 ml) were placed in the reaction vessel, then shaken twice at room temperature for 60 minutes to effect coupling, and thereafter dried, whereby 0.6 g of Fmoc-Ala-Asn-Asn-Glu(OBut)-Ile-Lys-(Boc)-Lys(Boc)-Wang-resin was obtained.

Then, 0.3 g of the Fmoc-Ala-Asn-Asn-Glu(OBut)-Ile-Lys(Boc)-Lys(Boc)-Wang-resin (content: 0.09 mmole) obtained above was placed in a reaction vessel and treated by following the solid phase synthesis steps as described below. The Fmoc group was removed with 20% PIP/DMF (steps 1–5) to protonate the amino group, and then the Fmoc-amino acid derivative was coupled in order by the DIPCI-HOBT method (steps 6, 7 and 8). The Fmoc-amino acid, DIPCI and HOBT were added and reacted, in step 6 as follows: Fmoc-Cys(Trt)-OH (157 mg, 0.3 mmole), HOBT (77 mg, 0.5 mmole) DIPCI (63 mg, 0.5 mmole) and NMP (6 ml) were placed in the reaction vessel and shaken twice at room temperature for 60 minutes to effect coupling. Fmoc-Asp(OBut)-OH (110 mg, 0.3 mmole), HOBT (77 mg, 0.3 mmole), DIPCI (63 mg, 0.5 mmole) and NMP (6 ml) were placed in the reaction vessel and shaken twice at room temperature for 60 minutes to effect coupling. Fmoc-Lys-(Boc)-OH (126 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Val-OH (92 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling.

Fmoc-Asp(OBut)-OH (110 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Val-OH (92 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Gln-OH (184 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Asp(OBut)-OH (110 mg, 0.5 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. After removing the Fmoc group with 20% PIP/DMF (steps 1–5) and drying, 0.39 g of H-Asp(OBut)-Gln-Val-Asp(OBut)-Val-Lys(Boc)-Asp(OBut)-Cys(Trt)-Ala-Asn-Asn-Glu(OBut)-Ile-Lys(Boc)-Lys(Boc)-Wang-resin was obtained. Then, 0.2 g of the peptide resin obtained above was suspended in a mixed solution of TFA (20 ml)—1,2-ethanedithiol (EDT) (0.6 ml)-PhOH (1.2 g) and shaken at room temperature for one hour, then the resin was filtered and washed 3 times with TFA (3 ml). The filtrate and the washings were collected, evaporated to dryness, and diethyl ether was added to the residue to form a precipitate, which was then filtered and dried to obtain 50 mg of a crude peptide.

Then, 23 mg of the crude peptide was purified by preparative HPLC using a μ-Bondasphere C 18 reversed phase column (1.9×15 cm). The crude peptide was dissolved in a small amount of acetic acid, then injected directly into the column and eluted under the condition of linear gradient of 10–16% (8 minute) acetonitrile/0.01N hydrochloric acid at a flow rate of 10 ml/min. The respective fractions were examined by analytical HPLC, and the fractions of high purity were collected and lyophilized to obtain 9 mg of H-Asp-Gln-Val-Asp-Val-Lys-Asp-Cys-Ala-Asn-Asn-Glu-Ile-Lys-Lys-OH. This peptide showed a single peak in analytical HPLC, and the results of amino acid analysis thereof were in good agreement with theoretical values: Asp, 4.91 (5); Glu, 2.28 (2); Ala, 1.09 (1); Val, 1.86 (2); Ile, 0.96 (1); Lys, 2.86 (3).

EXAMPLE 2

Preparation of Triacontapeptide of Formula II

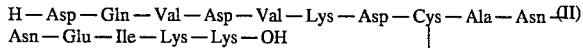
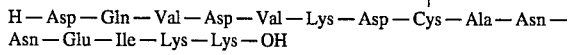

A 10 mg portion of the crude peptide (H-Asp-Gln-Val-Asp-Val-Lys-Asp-Cys-Ala-Asn-Asn-Glu-Ile-Lys-Lys-OH) obtained in Example 1 was dissolved in 1 ml of water, then adjusted to pH 8 with potassium hydrogencarbonate, and stirred at room temperature for two days to form a symmetrical disulfide linkage. After lyophilization, the dried product was dissolved in a small amount of acetic acid, then injected directly into a μ-Bondasphere C 18 reversed phase column (1.9×15 cm) and eluted under the condition of linear gradient of 11–15% (8 minutes) acetonitrile/0.01N hydrochloric acid at a flow rate of 10 ml/min. The respective fractions were examined by analytical HPLC. The fractions of high purity were collected and lyophilized to obtain 3 mg of

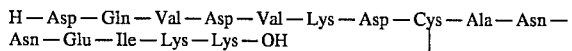
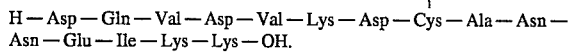

The peptide thus obtained showed a single peak in analytical

HPLC. The results of amino acid analysis were in good agreement with theoretical values: Asp, 4.81 (5); Glu, 2.18 (2); Ala, 0.99 (1); Val, 1.76 (2); Ile, 0.86 91); Lys, 2.76 (3).

EXAMPLE 3

Preparation of Pentadecapeptide of Formula III

H-Gly-Val-Leu-Ala-Cys-Ala-Ile-Ala-Thr-His-Ala-Lys-Ile-Arg-Asp-OH (III)

In a reaction vessel was placed 0.5 g of Fmoc-Asp(OBut)-Wang-resin (content: 0.32 mmole/0.5 g) and treated by following the solid phase synthesis steps as described below. The Fmoc group was removed with 20% PIP/DMF (steps 1–5) to protonate the amino group, and then the Fmoc-amino acid derivative was coupled in order by the DIPCI-HOBT method (steps 6, 7 and 8). The Fmoc-amino acid, DIPCI and HOBT were added and reacted, in step 6 as follows: Fmoc-Arg(Mtr)-OH (779 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ile-OH (452 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Lys(Boc)-OH (600 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ala-OH (398 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-His(Trt)-OH (793 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Thr(But)-OH (508 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ala-OH (398 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ile-OH (452 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ala-OH (398 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Cys(Trt)-OH (593 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Ala-OH (398 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Leu-OH (452 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Val-OH (435 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. Fmoc-Gly-OH (380 mg, 1.3 mmoles), HOBT (190 mg, 1.3 mmoles), DIPCI (163 mg, 1.3 mmoles) and NMP (6 ml) were placed in the reaction vessel and shaken twice at room temperature for 60 minutes to effect coupling. After removal of the Fmoc group with 20% PIP/DMF (steps 1–5) and drying, 1.2 g of H-Gly-Val-Leu-Ala-Cys(Trt)-Ala-Ile-Ala-Thr(But)-His(Trt)-Ala-Lys (Boc)-Ile-Arg(Mtr)-Asp(OBut)-Wang-resin was obtained. A 0.25 g portion of the peptide resin obtained above was suspended and shaken in a mixed solution of TFA (20 ml)—EDT (0.6 ml)—PhOH (1.2 g) at room temperature for 6 hours. Then the resin was filtered and washed 3 times with 3 ml of TFA. The filtrate and the washings were collected and evaporated to dryness. Diethyl ether was added to the residue to form a precipitate, which was filtered and dried to obtain 85 mg of a crude peptide.

The crude peptide, weighing 85 mg, was purified by preparative HPLC using a μ-Bondasphere C 18 reversed phase column (1.9×15 cm). The crude peptide was dissolved in a small amount of acetic acid, then injected directly into the column and eluted under the condition of linear gradient of 16–24% acetonitrile/0.01N hydrochloric acid at a flow rate of 10 ml/min. The respective fractions were examined by analytical HPLC, and the fractions of high purity were collected and lyophilized to obtain 27 mg of H-Gly-Val-Leu-Ala-Cys-Ala-Ile-Ala-Thr-His-Ala-Lys-Ile-Arg-Asp-OH. The peptide showed a single peak in analytical HPLC, and the results of amino acid analysis thereof were in good agreement with the theoretical values: Asp, 1.16 (1); Gly, 1.12 (1); His, 0.98 (1); Arg, 1.02 (1); Thr, 1.09 (1); Ala, 3.79 (4); Val, 0.98 (1); Ile, 1.91 (2); Leu, 1.02 (1); Lys, 0.89 (1).

EXAMPLE 4

Preparation of Triacontapeptide of Formula IV

H—Gly—Val—Leu—Ala—Cys—Ala—Ile—Ala—Thr—His—Ala— (IV)
Lys—Ile—Arg—Asp—OH |
                    |
H—Gly—Val—Ala—Cys—Ala—Ile—Ala—Thr—His—Ala—
Lys—Ile—Arg—Asp—OH

An 8 mg portion of the peptide (H-Gly-Val-Leu-Ala-Cys-Ala-Ile-Ala-Thr-His-Ala-Lys-Ile-Arg-Asp-OH) obtained in Example 3 was dissolved in 1 ml of water, then adjusted to pH 8 with potassium hydrogencarbonate, and stirred at room temperature for 2 days to form a symmetrical disulfide linkage. After lyophilization, the dried product was dissolved in a small amount of acetic acid, then injected directly into a μ-Bondasphere C 18 reversed phase column (1.9×15 cm) and eluted under the condition of linear gradient of 20–23% (8 minutes) acetonitrile/0.01N hydrochloric acid at a flow rate of 10 ml/min. The respective fractions were examined by analytical HPLC, and the fractions of high purity were collected and lyophilized to obtain 3.6 mg of

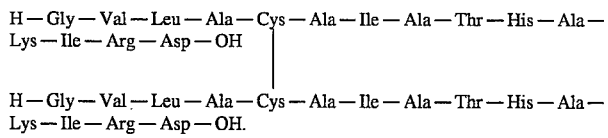

The peptide showed a single peak in analytical HPLC. The results of amino acid analysis thereof were in good agreement with theoretical values: Asp, 1.16 (1); Gly, 1.02 (1); His, 1.08 (1); Arg, 1.12 (1); Thr, 0.99 (1); Ala, 3.89 (4); Val, 1.08 (1); Ile, 1.81 (2); Leu, 0.92 (1); Lys, 0.99 (1).

EXAMPLE 5

Preparation of Triacontapeptide of Formula V

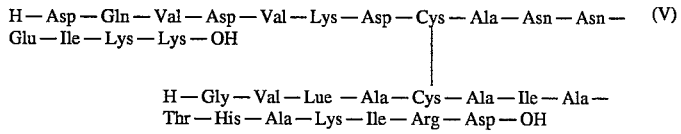

A 0.3 g portion of the intermediate of Example 1, namely Fmoc-Ala-Asn-Asn-Glu(OBut)-Ile-Lys(Boc)-Lys (Boc)-Wang-resin (content: 0.09 mmole) was placed in a reaction vessel and treated by following the solid phase synthesis steps as described below. The Fmoc group was removed with 20% PIP/DMF (steps 1–5) to protonate the amino group, and then the Fmoc-amino acid derivative was coupled in order by the DIPCI-HOBT method (steps 6.7 and 8). The Fmoc-amino acid, DIPCI and HOBT were added and reacted, in step 6 as follows: Fmoc-Cys(But)-OH (108 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Asp(OBut)-OH (110 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Lys(Boc)-OH (126 mg, 0.3 mmole) HOBT (77 mg, 0.5 mmole), DIPCI (63 mg, 0.5 mmole) and NMP (6 ml) ere placed in the reaction vessel and shaken twice at room temperature for 60 minutes to effect coupling. Fmoc-Val-OH (92 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Asp (OBut)-OH (110 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Val-OH (92 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Fmoc-Gln-OH (100 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. Boc-Asp(OBut)-OH (80 mg, 0.3 mmole), HOBT (77 mg, 0.5 mmole), DIPCI (63 mg, 0.5 mmole) and NMP (6 ml) were placed in the reaction vessel and shaken twice at room temperature for 60 minutes to effect coupling. After drying, 0.35 g of Boc-Asp(OBut)-Gln-Val-Asp(OBut)-Val-Lys-(Boc)-Asp(OBut)-Cys(But)-Ala-Asn-Asn-Glu(OBut)-Ile-Lys(Boc)-Lys(Boc)-Wang-resin was obtained.

The peptide resin obtained above (88 mg, 0.04 mmole) was twice suspended and shaken at room temperature in a solution of 3-nitropyridinesulfenyl chloride (38 mg, 0.2 mmole) in acetic acid (2 ml) to effect reaction. The reaction product was washed with acetic acid (2 ml), NMP (2 ml) and further methanol (2 ml), and then dried to obtain yellow Boc-Asp(OBut)-Gln-Val-Asp(OBut)-Val-Lys (Boc)-Asp(OBut)-Cys(Npys)-Ala-Asn-Asn-Glu(OBut)-Ile-Lys-(Boc)-Lys(Boc)-Wang-resin.

The peptide resin thus obtained was twice suspended and shaken in a mixed solution of TFA (1.8 ml)—PhOH (0.2 g) at room temperature for 30 minutes, then the resin was filtered and washed 3 times with TFA (2 ml). The filtrate and the washings were collected, evaporated to dryness and diethyl ether was added to the dried residue to form a precipitate. The precipitate was collected by filtration and dried to obtain 70 mg of a crude peptide (H-Asp-Gln-Val-Asp-Val-Lys-Asp-Cys(Npys)-Ala-Asn-Asn-Glu-Ile-Lys-Lys-OH).

The crude peptide was purified by preparative HPLC using a μ-Bondasphere C 18 reversed phase column (1.9×15 cm). The crude peptide was dissolved in a small amount of acetic acid, then injected directly into the column, and eluted under the condition of linear gradient of 16–23% acetonitrile 0.01N hydrochloric acid at a flow rate of 10 ml/min. The respective fractions were examined by analytical HPLC, and the fractions of high purity were collected and lyophilized to obtain 30 mg of H-Asp-Gln-Val-Asp-Val-Lys-Asp-Cys(Npys)-Ala-Asn-Asn-Glu-Ile-Lys-Lys-OH. The peptide thus obtained showed a single peak in analytical HPLC. The peptide (9.3 mg, 0.005 mmole) and H-Gly-Val-Leu-Ala-Cys-Ala-Ile-Ala-Thr-His-Ala-Lys-Ile-Arg-Asp-OH (7.7 mg, 0.005 mmole) obtained in Example 3 were dissolved in water (0.5 ml), and the solution was adjusted to pH 8 with potassium hydrogencarbonate and then stirred at room temperature for one hour to form an unsymmetrical disulfide linkage. After lyophilized, the dried product was dissolved in a small amount of acetic acid, then injected directly into a μ-Bondasphere C 18 reversed phase column (1.9×15 cm) and eluted under the condition of linear gradient of 15– 23% (8 minutes) acetonitrile/0.01N hydrochloric acid at a flow rate of 10 ml/min. The respective fractions were examined by analytical HPLC and the fractions of high purity were collected and lyophilized to obtain 3.4 mg of H—Asp—Gln—Val—Asp—Val—Lys—Asp—Cys—Ala—Asn—Asn—
Glu—Ile—Lys—Lys—OH
                                          |
                  H—Gly—Val—Leu—Ala—Cys—Ala—Ile—Ala—
                  Thr—His—Ala—Lys—Ile—Arg—Asp—OH.

The peptide showed a single peak in analytical HPLC. The results of amino acid analysis thereof were in good agreement with theoretical values: Asp, 5.87 (6); Glu, 2.20 (2); Gly, 1.21 (1); His, 1.03 (1); Arg, 0.91 (1); Thr, 1.01 (1); Ala, 4.90 (5); Val, 2.79 (3); Ile, 2.82 (3); Leu, 0.99 (1); Lys, 4.07 (4).

EXAMPLE 6

Blast formation of lymphocytes by peptides of formula I–V of the present invention Peripheral blood lymphocytes collected from a mite-allergic patient or a non-allergic subject were suspended in a cell culture medium RPMI 1640 supplemented with 10% fetal bovine serum, so as to give a suspension of $1 \times 10^6$ cells/ml. Then, the suspension (0.2 ml/well) prepared above was placed in a 96-well microplate for cell culture and further, 20 μl each of a solution of one of the peptides of the formula I–V was placed in the respective wells. The lymphocytes thus treated were cultivated in a humidified atmosphere containing 5% $CO_2$ at 37° C. for 7 days. Thereafter, 20 μl of a $^3$H-thymidine solution (12.5 μCi/ml) was added to each of the wells and allowed to react overnight. The peripheral blood lymphocytes were then collected onto filter, and the radioactivity was measured by a liquid scintillation counter. The results thus obtained are shown Table 1.

As is apparent from Table 1, virtually no incorporation of $^3$H-thymidine was recognized in the peripheral blood lymphocyte of a non-allergic subject, while a high radioactivity was detected from the peripheral blood lymphocytes of a mite-allergic patient. This demonstrates that the lymphocytes of a patient sensitized by mites underwent blast formation by the action of the peptide of the present invention.

TABLE 1

| Peptide | Specimen 1 | Specimen 2 | Specimen 3 | Specimen 4 |
|---|---|---|---|---|
| I | 281 | 389 | 282 | <100 |
| II | 219 | 125 | 158 | <100 |
| III | 547 | 259 | 158 | <100 |
| IV | 374 | 324 | 162 | <100 |
| V | 1457 | 430 | 179 | <100 |

Note:
1) Specimens 1–3 were prepared from the lymphocytes of mite-allergic patients. Specimen 4 was prepared from the lymphocytes of a non-allergic subject.
2) The values in the Table indicate the radioactivity of $^3$H-thymidine incorporated into lymphocytes, expressed in cpm.

We claim:

1. A peptide which causes the blast formation of lymphocytes sensitized by mites, wherein said peptide is selected from the group consisting of peptides of formula (I)(SEQ ID NO:1), formula II), formula (III)(SEQ ID NO:2), formula (IV), and formula (V):

H—Asp—Gln—Val—Asp—Val—Lys—Asp-
—Cys—Ala—Asn—
Asn—Glu—Ile—Lys—Lys—OH     (I)

H—Asp—Gln—Val—Asp—Val—Lys—Asp—Cys—Ala—(II)Asn—
Asn—Glu—Ile—Lys—Lys—OH
|
H—Asp—Gln—Val—Asp—Val—Lys—Asp—Cys—Ala—Asn—
Asn—Glu—Ile—Lys—Lys—OH

H—Gly—Val—Leu—Ala-     (III)
—Cys—Ala—Ile—Ala—Thr—His—
Ala—Lys—Ile—Arg—Asp—OH

H—Gly—Val—Leu—Ala—Cys—Ala—Ile—Ala—Thr—(IV)—
Ala—Lys—Ile—Arg—Asp—OH
\
H——Gly——Val—Leu—Ala—Cys—Ala—Ile—Ala—Thr—
His—Ala—Lys—Ile—Arg—Asp—OH

H—Asp—Gln—Val—Asp—Val—Lys—Asp—Cys—Ala—(V)Asn—
Asn—Glu—Ile—Lys—Lys—OH
/
H——Gly——Val——Leu——Ala——Cys—Ala—Ile—
Ala—Thr—His—Ala—Lys—Ile—Arg—Asp—OH wherein said peptide is part of the Der f II allergen of *Dermatophagoides farinae*.

2. The peptide according to claim 1 which is a pentadecapeptide represented by the formula (I)

H-Asp-Gln-Val-Asp-Val-Lys-Asp-Cys-Ala-Asn-Asn-Glu-Ile-Lys-Lys-OH    (I)

wherein Asp, Gln, Val, Lys, Cys, Ala, Asn, Glu and Ile denote, respectively, the residue of aspartic acid, glutamine, valine, lysine, cysteine, alanine, asparagine, glutamic acid and isoleucine.

3. The peptide according to claim 1 which is a triacontapeptide represented by the formula (II)

H—Asp—Gln—Val—Asp—Val—Lys—Asp—Cys—Ala—Asn—(II)
Asn—Glu—Ile—Lys—Lys—OH
|
H—Asp—Gln—Val—Asp—Val—Lys—Asp—Cys—Ala—Asn—
Asn—Glu—Ile—Lys—Lys—OH wherein Asp, Gln, Val, Lys, (Cys)$_2$, Ala, Asn, Glu and Ile denote, respectively, the residue of aspartic acid, glutamine, valine, lysine, cystine, alanine, asparagine glutamic acid and isoleucine.

4. The peptide according to claim 1 which is a pentadecapeptide represented by the formula (III)

H-Gly-Val-Leu-Ala-Cys-Ala-Ile-Ala-Thr-His-Ala-Lys-Ile-Arg-Asp-OH    (III)

wherein Gly, Asp, Val, Lys, Cys, Ala, Ile, Leu, Thr, His and Arg denote, respectively, the residue of glycine, aspartic acid, valine, lysine, cysteine, alanine, isoleucine, leucine, threonine, histidine and arginine.

5. The peptide according to claim 1 which is a triacontapeptide represented by the formula (IV)

H—Gly—Val—Leu—Ala—Cys—Ala—Ile—Ala—Thr—His—Ala—    (IV)
Lys—Ile—Arg—Asp—OH
|
H—Gly—Val—Ala—Cys—Ala—Ile—Ala—Thr—His—Ala—
Lys—Ile—Arg—Asp—OH wherein Gly, Asp, Val, Lys, (Cys)$_2$, Ala, Ile, Leu, Thr, His and Arg denote, respectively, the residue of glycine, aspartic acid, valine, lysine, cystine, alanine, isoleucine, leucine, threonine, histidine and arginine.

6. The peptide according to claim 1 which is a triacontapeptide represented by the formula (V)

H—Asp—Gln—Val—Asp—Val—Lys—Asp—Cys—Ala—Asn—(V)
Asn—Glu—Ile—Lys—Lys—OH
/
H—Gly—Val—Leu—Ala—Cys—Ala—Ile—Ala—Thr—His—
Ala—Lys—Ile—Arg—Asp—OH wherein Asp, Gln, Val, Lys, (Cys)$_2$, Ala, Asn, Glu, Ile, Gly, Leu, Thr, His and Arg denote, respectively, the residue of aspartic acid, glutamine, valine, lysine, cystine, alanine, asparagine, glutamic acid, isoleucine, glycine, leucine, threonine, histidine and arginine.

7. A diagnostic agent for mite allergy which comprises the peptide according to claim 1.

8. A method of diagnosing allergy to mites of the genus *Dermatophagoides* in a patient, said method comprising separately exposing lymphocytes from said patient to each of the peptides of formulas (I) to (V):

H—Asp—Gln—Val—Asp—Val—Lys—Asp-     (I)
—Cys—Ala—Asn—
Asn—Glu—Ile—Lys—Lys—OH

H—Asp—Gln—Val—Asp—Val—Lys—Asp—Cys—Ala—(II)Asn—
Asn—Glu—Ile—Lys—Lys—OH
|
H—Asp—Gln—Val—Asp—Val—Lys—Asp—Cys—Ala—Asn—
Asn—Glu—Ile—Lys—Lys—OH

H—Gly—Val—Leu—Ala-     (III)
—Cys—Ala—Ile—Ala—Thr—His—
Ala—Lys—Ile—Arg—Asp—OH

H—Gly—Val—Leu—Ala—Cys—Ala—Ile—Ala—Thr—(IV)—
Ala—Lys—Ile—Arg—Asp—OH
\
H——Gly——Val—Leu—Ala—Cys—Ala—Ile—Ala—Thr—
His—Ala—Lys—Ile—Arg—Asp—OH

H—Asp—Gln—Val—Asp—Val—Lys—Asp—Cys—Ala—(V)Asn—
Asn—Glu—Ile—Lys—Lys—OH
/
H——Gly——Val——Leu——Ala——Cys—Ala—Ile—
Ala—Thr—His—Ala—Lys—Ile—Arg—Asp—OH adding radioactive labelled thymidine, and measuring the radioactive labelled thymidine incorporated in said lymphocytes.

* * * * *